United States Patent
Schwab et al.

(10) Patent No.: US 6,538,168 B1
(45) Date of Patent: *Mar. 25, 2003

(54) PREPARATION OF C5-/C6-OLEFINS

(75) Inventors: Peter Schwab, Bad Dürkheim (DE); Michael Schulz, Ludwigshafen (DE); Ralf Schulz, Speyer (DE); Sylvia Huber, Zwingenberg (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

This patent is subject to a terminal disclaimer.

(21) Appl. No.: 09/610,942

(22) Filed: Jul. 6, 2000

(30) Foreign Application Priority Data

Jul. 12, 1999 (DE) .......................... 199 32 060

(51) Int. Cl.[7] .................................. C07C 6/02
(52) U.S. Cl. ................. 585/647; 585/324; 585/643; 585/646
(58) Field of Search ................. 585/324, 643, 585/646, 647

(56) References Cited

U.S. PATENT DOCUMENTS

| 3,590,096 A | * | 6/1971 | Banks ............... 585/314 |
| 3,595,920 A | | 7/1971 | Ellis et al. ............ 585/646 |
| 3,646,143 A | | 2/1972 | Ellis et al. ............ 585/191 |
| 5,057,638 A | | 10/1991 | Sweeney ............... 585/324 |
| 5,304,692 A | * | 4/1994 | Yamada et al. ......... 585/646 |
| 6,166,279 A | * | 12/2000 | Schwab et al. ......... 585/312 |

FOREIGN PATENT DOCUMENTS

| CA | 2249019 | 4/1999 |
| DE | 197 46 040 | 4/1999 |
| EP | 0 945 415 | 9/1999 |

* cited by examiner

Primary Examiner—Thuan D. Dang
(74) Attorney, Agent, or Firm—Keil & Weinkauf (57) ABSTRACT

A process for preparing $C_5/C_6$-olefins from an olefinic starting stream comprising $C_4$-hydrocarbons comprises a) carrying out a metathesis reaction in the presence of a metathesis catalyst so as to convert the 1-butene, 2-butene and isobutene present in the starting stream into a mixture of $C_2$–$C_6$-olefins and butanes, b) firstly fractioning the resulting product stream by distillation to give a low boiler fraction A comprising $C_2$–$C_4$-olefins and butanes or $C_2$–$C_3$-olefins, which is discharged, and a high boiler fraction comprising $C_4$–$C_8$-olefins and butanes, c) fractioning the high boiler fraction from b) by distillation to give a low boiler fraction B comprising butenes and butanes, an intermediate boiler fraction C comprising pentene and methylbutene and a high boiler fraction D comprising hexane and methylpentene, d) where all or part of the fraction B and/or C are recirculated to the process step a) and the fraction D is discharged as product.

9 Claims, 3 Drawing Sheets

PREPARATION OF C5-/C6-OLEFINS

The present invention relates to a process for converting olefinic $C_4$-hydrocarbons, for example from steam crackers or FCC plants, into pentenes and hexenes by means of a metathesis reaction. Propene is obtained as desired process coproduct.

Olefinic metathesis (disproportionation) describes, in its simplest form, the reversible, metal-catalyzed transalkylidenation of olefins by rupture and reformation of C=C double bonds in accordance with the following equation:

In the special case of the metathesis of acyclic olefins, a distinction is made between self-metathesis in which one olefin is transformed into a mixture of two olefins of differing molar mass (for example: propene→ethene+2-butene) and cross-metathesis or co-metathesis which describes the reaction of two different olefins (propene+1-butene→ethene+2-pentene). If one of the reactants is ethene, this is generally referred to as an ethenolysis.

Suitable metathesis catalysts are, in principle, homogeneous and heterogeneous transition metal compounds, in particular from transition groups VI to VIII of the Periodic Table of the Elements, and also homogeneous and heterogeneous catalyst systems in which these compounds are present.

Various metathesis processes starting from $C_4$ streams have been described.

U.S. Pat. No. 5,057,638 relates to a process for preparing 1-hexene, comprising the process steps:

a) metathesis of 1-butene to give a mixture of 3-hexene and ethene, b) separation of the 3-hexene from the product mixture obtained in step a), c) reaction of the 3-hexene with an electrophile containing reactive hydrogen, preferably derived from water or carboxylic acid, under acid conditions which allow the addition of the electrophilic components onto the C=C bond (e.g. hydration), and d) cracking of the product from step c), e.g. by dehydration, to prepare a mixture of n-hexenes in which 1-hexene is present in economically acceptable amounts.

U.S. Pat. Nos. 3,646,143 and 3,595,120 (May 5, 1969), Gulf Res. & Dev.Co. describes the conversion of short-chain $C_4$–$C_{12}$-olefins (preferably α-olefins) into higher olefins by metathesis. The process comprises bringing the starting olefin into contact with a catalyst comprising aluminum, molybdenum or rhenium and silver or copper at from 100 to 240° C., with relatively low-boiling by-products, e.g. ethene, being able to be removed from the equilibrium in situ.

The present invention further relates to a combined process for preparing $C_5/C_6$-olefins together with propene as secondary product from $C_4$ fractions from steam crackers or FCC plants.

Steam crackers represent the main source of basic petrochemicals, for example ethene, propene, $C_4$-olefins and higher hydrocarbons. In the cracking process, it is necessary to introduce large amounts of energy at high temperatures within a time which is sufficient for cracking to occur but does not allow further reaction of the cracking products. In the cracking of hydrocarbons, the yield of ethene and propene is therefore determined essentially by

- the type of hydrocarbons used (naphtha, ethane, LPG, gas oil, or the like),
- the cracking temperature,
- the residence time
- and the partial pressures of the respective hydrocarbons.

The highest yield of ethene and propene is achieved at cracking temperatures of from 800 to 850° C. and residence times of from 0.2 to 0.5 s. In this range the main product is always ethene, and the $C_3/C_2$ product ratio can be increased from about 0.5 to 0.7 by slight variation in the cracking conditions. The world-wide demand for propene is increasing more rapidly than that for ethene. This has the consequence, inter alia, that processes for downstream utilization of the higher hydrocarbons formed in the cracking process, e.g. $C_4$-hyrocarbons, are gaining increasing importance in respect of the optimization of the propene yield.

It is an object of the present invention, in the context of work on improving the value added derived from steam cracker by-products, to develop a flexibly controllable catalytic process for obtaining pure $C_5$-/$C_6$-olefin streams from inexpensive olefin-containing $C_4$-hydrocarbon mixtures without introduction of ethene.

We have found that this object is achieved by a process for preparing $C_5$-/$C_6$-olefins from an olefinic starting stream comprising $C_4$-hydrocarbons, which comprises a) carrying out a metathesis reaction in the presence of a metathesis catalyst comprising at least one compound of a metal of transition group VIb, VIIb or VIII of the Periodic Table of the Elements so as to convert the 1-butene, 2-butene and isobutene present in the starting stream into a mixture of $C_2$–$C_6$-olefins and butanes, b) firstly fractionating the resulting product stream by distillation to give a low boiler fraction A comprising $C_2$–$C_4$-olefins and butanes, which is discharged, and a high boiler fraction comprising $C_4$–$C_6$-olefins and butanes, c) subsequently fractionating the high boiler fraction from b) by distillation to give a low boiler fraction B comprising butenes and butanes, an intermediate boiler fraction C comprising pentene and methylbutene and a high boiler fraction D comprising hexene and methylpentene, d) where all or part of the fractions B and/or C are recirculated to the process step a) and the fraction D is discharged as product.

The expression "comprising" allows for the presence of relatively small amounts of other hydrocarbons.

In this process, carried out in a single stage, a fraction comprising $C_4$-olefins, preferably n-butenes, isobutene and butanes is converted over a homogeneous or preferably heterogeneous metathesis catalyst into a product mixture of (inert) butanes, unreacted 1-butene, 2-butene and possibly isobutene and also the metathesis products ethene, propene, 2-pentene, possibly 2-methyl-2-butene, 3-hexene and possibly 2-methyl-2-pentene in a metathesis reaction according to the following equation:

The amount of branched $C_5$- and $C_6$-hydrocarbons in the metathesis product depends on the isobutene content of the $C_4$ feed and is preferably kept as small as possible (<3%).

To explain the process of the present invention in its different variations in more detail, the above equilibrium reaction (without taking isobutene into account) will be divided into three important individual reactions:

1. Cross-metatathiesis of 1-butene with 2-butene

2. Self-metalhesis of 1-butene

3. Ethenolysis of 2-butene

Depending on the prevailing demand for the target products propene, 2-pentene and 3-hexene (the term 2-pentene includes any isomers formed, e.g. cis/trans or 2-methyl-2-butene, and the same applies analogously to 3-hexene), the external mass balance of the process can be influenced in a targeted manner by shifting the equilibrium by recirculation of particular substreams. Thus, for example, the 3-hexene yield is increased when the cross-metathesis of 1-butene with 2-butene is suppressed by recirculation of 2-pentene into the metathesis step, so that very little, if any, 1-butene is consumed by the cross-metathesis. The self-metathesis of 1-butene to 3-hexene which then proceeds preferentially forms additional ethene which reacts in a subsequent reaction with 2-butene to form the desired product propene.

Olefin mixtures comprising 1-butene, 2-butene and isobutene are obtained, inter alia, in various cracking processes such as steam cracking or FCC as $C_4$ fraction. Alternatively, it is possible to use butene mixtures as are obtained in the dehydrogenation of butenes or by dimerization of ethene. Butanes present in the $C_4$ fraction behave as inerts. Dienes, alkynes or enynes are removed before the metathesis step of the present invention by means of customary methods such as extraction or selective hydrogenation.

The butene content of the $C_4$ fraction used in the process is from 1 to 100% by weight, preferably from 60 to 90% by weight. The butene content refers to 1-butene, 2-butene and isobutene.

Preference is given to using a $C_4$ fraction as is obtained in steam cracking or FCC or in the dehydrogenation of butane.

Raffinate I or II can be used as $C_4$ fraction, and the $C_4$ stream is freed of interfering impurities prior to the metathesis reaction by appropriate treatment over protective adsorber beds, preferably over high surface area aluminum oxides or molecular sieves.

The low boiler fraction A obtained, in particular the $C_{2/3}$ fraction, can be directly processed further as such, fed to the work-up sequence of a steam cracker or FCC plant in order to obtain pure ethene and propene, or recirculated completely or in part to the metathesis step in order to increase the yield of pentene/hexene, or be used separately for the isolation of ethene and propene as pure component (in particular as $C_{2/3}$ fraction).

The metathesis reaction is preferably carried out in the presence of heterogeneous, not or only slightly isomerization-active metathesis catalysts selected from the class consisting of transition metal compounds of metals of groups VIb, VIIb and VIII of the Periodic Table of the Elements applied to inorganic supports.

The preferred metathesis catalyst is rhenium oxide on a support, preferably on γ-aluminum oxide or on $Al_2O_3/B_2O_3/SiO_2$ mixed supports.

Particular preference is given to using $Re_2O_7/\gamma\text{-}Al_2O_3$ having a rhenium oxide content of from 1 to 20%, preferably from 3 to 15%, particularly preferably from 6 to 12% (% by weight), as catalyst.

In the case of a liquid-phase process, the metathesis is preferably carried out at from 0 to 150° C., particularly preferably from 20 to 80° C., and a pressure of from 2 to 200 bar, particularly preferably from 5 to 30 bar.

When the metathesis is carried out in the gas phase, the temperature is preferably from 20 to 300° C., particularly preferably from 50 to 200° C. The pressure in this case is preferably from 1 to 20 bar, particularly preferably from 1 to 5 bar.

A further object of the invention, in the context of work on improving the value added to steam cracker by-products, is to develop a flexibly controllable process sequence of utilizing a $C_4$ fraction. The objective is to add value by converting $C_4$-olefins into higher-priced olefin fractions. Crude $C_4$ fraction from steam crackers or FCC plants is available as feedstock.

We have found that this object is achieved by a process for preparing $C_5/C_6$-olefins and propene from steam cracker or refinery $C_4$ streams, comprising the substeps (1) removal of butadiene and acetylenic compounds by, if desired, extracting butadiene with a butadiene-selective solvent and subsequently or alternatively selectively hydrogenating butadienes and acetylenic impurities present in the crude $C_4$ fraction to give a reaction product comprising n-butenes and isobutene and essentially no butadienes and acetylenic compounds, (2) removal of isobutene by reacting the reaction product from the preceding stage with an alcohol in the presence of an acid catalyst to give an ether, and separating off the ether and the alcohol either simultaneously with or after the etherification to give a reaction product comprising n-butenes and possibly oxygen-containing impurities, where the ether formed can be discharged or redissociated to obtain pure isobutene and the etherification step can be followed by a distillation step for separating off isobutene, where, if desired, introduced $C_3$-, i-$C_4$- and $C_5$-hydrocarbons can be removed by distillation in the work-up of the ether, or oligomerizing or polymerizing isobutene from the reaction product from the preceding step in the presence of an acid catalyst whose acid strength is suitable for selectively separating off isobutene as oligoisobutene or polyisobutene to give a stream containing from 0 to 15% of residual isobutene, (3) removal of the oxygen-containing impurities from the product of the preceding steps over appropriately selected adsorber materials, (4) metathesis of the resulting raffinate II stream as described.

The substep of selective hydrogenation of butadiene and acetylenic impurities present in the crude $C_4$ fraction is preferably carried out in two stages by bringing the crude $C_4$ fraction into contact with a catalyst comprising at least one metal selected from the group consisting of nickel, palladium and platinum on a support, preferably palladium on aluminum oxide, in the liquid phase at from 20 to 200° C., a pressure of from 1 to 50 bar, a volume flow of from 0.5 to 30 m$^3$ of fresh feed per m$^3$ of catalyst per hour and a ratio of recycle to feed stream of from 0 to 30 at a molar ratio of hydrogen to diolefins of from 0.5 to 50 to give a reaction product in which, apart from isobutene, the n-butenes 1-butene and 2-butene are present in a molar ratio of from 2:1 to 1:10, preferably from 2:1 to 1:2, and in which essentially no diolefins and acetylenic compounds are present.

The substep of butadiene extraction from crude $C_4$ fraction is preferably carried out using a butadiene-selective solvent selected from the class consisting of polar aprotic solvents such as acetone, furfural, acetonitrile, dimethylacetamide, dimethylformamide and N-methylpyrrolidone to give a reaction product in which the n-butenes 1-butene and 2-butene are present in a molar ratio of from 2:1 to 1:10, preferably from 2:1 to 1:2.

The substep of isobutene etherification is preferably carried out in a three-stage reactor cascade using methanol or isobutanol, preferably isobutanol in the presence of an acid ion exchanger, in which the extraction mixture flows from the top downward through the flooded fixed-bed catalyst, where the reactor inlet temperature is from 0 to 60° C., preferably from 10 to 50° C., the outlet temperature is from 25 to 85° C., preferably from 35 to 75° C., the pressure is from 2 to 50 bar, preferably from 3 to 20 bar and the ratio of isobutanol to isobutene is from 0.8 to 2.0, preferably from 1.0 to 1.5, and the total conversion corresponds to the equilibrium conversion.

The substep of isobutene removal is preferably carried out by oligomerization or polymerization of isobutene starting from the reaction product obtained from the above-described step of butadiene extraction and/or selective hydrogenation and in the presence of a catalyst selected from the class consisting of homogeneous and heterogeneous Bronsted acids, preferably heterogeneous catalysts comprising an oxide of a metal of transition group VIb of the Periodic Table of the Elements and an acidic inorganic support, preferably $WO_3TiO_2$, to produce a stream having a residual isobutene content of less than 15%.

Selective Hydrogenation of Crude $C_4$ Fraction

Alkynes, alkynenes and alkadienes are, owing to their tendency to polymerize or their pronounced tendency to form complexes with transition metals, undesirable substances in many industrial syntheses. They sometimes have a very strong adverse effect on the catalysts used in these reactions.

The $C_4$ stream from a steam cracker contains a high proportion of multiply unsaturated compounds such as 1,3-butadiene, 1-butyne (ethylacetylene) and butenine (vinylacetylene). Depending on the downstream processing, the multiply unsaturated compounds are either extracted (butadiene extraction) or selectively hydrogenated. In the former case, the residual content of multiply unsaturated compounds is typically from 0.05 to 0.3% by weight, while in the latter case it is typically from 0.1 to 4.0% by weight. Since the residual amounts of multiply unsaturated compounds likewise interfere in further processing, a further purification by selective hydrogenation to values of <10 ppm is necessary. To obtain the highest possible proportion of valuable butenes, overhydrogenation to butanes should be kept as low as possible.

Suitable hydrogenation catalysts are described in:

J. P. Boitiaux, J. Cosyns, M. Derrien and G. Lèger, Hydrocarbon Processing, March 1985, p.51–59

Description of bimetallic catalysts for selective hydrogenations of $C_2$-, $C_3$-, $C_4$-, $C_5$- and $C_{5+}$-hydrocarbon streams. Particularly bimetallic catalysts comprising group VIII and group IB metals display improvements in selectivity compared to supported, pure Pd catalysts.

DE-A-2 059 978

Selective hydrogenation of unsaturated hydrocarbons in the liquid phase over a Pd/alumina catalyst. To produce the catalyst, the alumina support having a BET surface area of 120 m$^2$/g is firstly subjected to a steam treatment at 110–300° C. and subsequently calcined at 500–1200° C. Finally, the Pd compound is applied and the catalyst is calcined at 300–600° C.

EP-A-0 564328 and EP-A-0 564 329

Catalyst comprising, inter alia, Pd and In or Ga on supports. The catalyst combination can be used without CO addition at high activity and selectivity.

EP-A-0 089 252

Supported Pd, Au catalysts.

Production of the catalyst comprises the following steps:

impregnation of a mineral support with a Pd compound calcination under $O_2$-containing gas treatment with a reducing agent impregnation with a halogenated Au compound treatment with a reducing agent washing-out of the halogen by means of a basic compound calcination under $O_2$-containing gas.

U.S. Pat. No. 5,475,173

Catalyst comprising Pd and Ag and alkali metal fluoride on an inorganic support.

Advantages of the catalyst: addition of KF gives increased butadiene conversion and better selectivity to butenes (i.e. reduced overhydrogenation to n-butane).

EP-A-0 653 243

In this catalyst, the active component is located predominantly in the mesopores and macropores. The catalyst also has a large pore volume and a low packing density. Thus, the catalyst from Example 1 has a packing density of 383 g/l and a pore volume of 1.17 ml/g.

EP-A-0 211 381
  Catalyst comprising a group VIII metal (preferably Pt) and at least one metal selected from among Pb, Sn or Zn on an inorganic support. The preferred catalyst comprises Pt/ZnAl$_2$O$_4$. The specified promoters Pb, Sn and Zn improve the selectivity of the Pt catalyst.

EP-A-0 722 776
  Catalyst comprising Pd and at least one alkali metal fluoride and, if desired, Ag on inorganic supports (Al$_2$O$_3$, TiO$_2$ and/or ZrO$_2$). The catalyst combination makes possible a selective hydrogenation in the presence of sulfur compounds.

EP-A-0 576 828
  Catalyst based on noble metal and/or noble metal oxide on Al$_2$O$_3$ supports having a defined X-ray diffraction pattern. The support comprises n-Al$_2$O$_3$ and/or γ-Al$_2$O$_3$. Owing to the specific support, the catalyst has high initial selectivity and can therefore be used immediately for the selective hydrogenation of unsaturated compounds.

JP 01110594
  Supported Pd catalyst
  A further electron donor is used in addition. This is either a metal deposited on the catalyst, for example Na, K, Ag, Cu, Ga, In, Cr, Mo or La, or an addition to the hydrocarbon feed, for example alcohol, ether or N-containing compounds. The measures described make it possible to achieve a reduction in the 1-butene isomerization.

DE-A-31 19 850
  Catalyst comprising SiO$_2$ or Al$_2$O$_3$ support having a surface area of from 10 to 200 m$^2$/g or $\leq$100 m$^2$/g and Pd and Ag as active components. The catalyst is employed primarily for the hydrogenation of hydrocarbon streams having a low butadiene content.

EP-A-0 780 155
  Catalyst comprising Pd and a group IB metal on an Al$_2$O$_3$ support, where at least 80% of the Pd and 80% of the group IB metal are applied in an external shell between r$_1$(=radius of the pellet) and 0.8-r$_1$.

Alternatively: Extraction of Butadiene from Crude C$_4$ Fraction

The preferred method of isolating butadiene is based on the physical principle of extractive distillation. Addition of selective organic solvents lowers the volatility of specific components of a mixture, in this case butadiene. These therefore remain together with the solvent in the bottoms from the distillation column, while the accompanying substances which could previously not be separated off by distillation can be removed at the top. The main solvents used for the extractive distillation are acetone, furfural, acetonitrile, dimethylacetamide, dimethylformamide (DMF) and N-methylpyrrolidone (NMP). Extractive distillations are particularly useful in the case of butadiene-rich C$_4$ fractions having a relatively high proportion of alkynes, for instance methylacetylene, ethylacetylene and vinylacetylene, and also methylallene.

The simplified principle of a solvent extraction of crude C$_4$ fraction can be described as follows: the completely vaporized C$_4$ fraction is fed in at the lower end of an extraction column. The solvent (DMF, NMP) flows downward from the top in countercurrent to the gas mixture and on its way down takes up the more readily soluble butadiene and small amounts of butenes. At the lower end of the extraction column, part of the pure butadiene isolated is introduced in order to strip out most of the butenes. The butenes leave the separation column at the top. In a further column, referred to as a degassing column, the butadiene is separated from the solvent by boiling and is subsequently distilled to recover it in pure form.

The reaction product of an extractive butadiene distillation is usually fed to the second stage of a selective hydrogenation in order to reduce the residual butadiene content to values of <10 ppm.

The C$_4$ steam remaining after removal of butadiene is referred to as C$_4$ raffinate or raffinate I and comprises mainly the components isobutene, 1-butene, 2-butene and also n-butane and isobutane.

Removal of Isobutene from Raffinate I

In the further fractionation of the C$_4$ stream, isobutene is then preferably isolated since it differs in terms of its branching and its higher reactivity from the remaining C$_4$ components. One possibility is removal by means of shape-selective molecular sieves, which makes it possible to isolate isobutene having a purity of 99% and in which the n-butenes and butane adsorbed in the pores of the molecular sieve can be desorbed again by means of a relatively high-boiling hydrocarbon, but the separation is usually carried out by distillation using a deisobutenizer by means of which isobutene is separated off together with 1-butene and isobutene at the top and 2-butenes and n-butane including residual amounts of isobutene and 1-butene remain in the bottoms, or extractively by reaction of isobutene with alcohols over acid ion exchangers. In the latter method, preference is given to using methanol (→MTBE) or isobutanol (IBTBE).

The preparation of MTBE from methanol and isobutene is carried out at from 30 to 100° C. and slightly superatmospheric pressure in the liquid phase over acid ion exchangers. It is carried out either in two reactors or in a two-stage shaft reactor in order to achieve virtually quantitative isobutene conversion (>99%). Due to the pressure-dependent formation of a methanol/MTBE azeotrope, the isolation of pure MTBE requires the use of a multistage pressure distillation or is achieved using more recent technology involving methanol adsorption on adsorbent resins. All other components of the C$_4$ fraction remain unchanged. Since small amounts of diolefins and acetylenes can shorten the life of the ion exchanger as a result of polymer formation, preference is given to using bifunctional Pd-containing ion exchangers over which only diolefins and acetylenes are hydrogenated in the presence of small amounts of hydrogen. This does not influence the etherification of the isobutene.

MTBE is used first and foremost for increasing the octane number of gasoline. As an alternative, MTBE and IBTBE can be redissociated in the gas phase at from 150 to 300° C. over acidic oxides to give pure isobutene.

A further possible way of removing isobutene from raffinate I is the direct synthesis of oligoisobutene/polyisobutene. Isobutene conversions of up to 95% can be achieved in this way over acidic homogeneous and heterogeneous catalysts, e.g. tungsten trioxide on titanium dioxide, to give a product stream having a residual isobutene content of not more than 5%.

Feed Purification of the Raffinate II Stream Over Adsorbent Materials

To improve the operating life of the catalysts used in the subsequent metathesis step, it is necessary, as described above, to use a feed purification step (guard bed) for removing catalyst poisons such as water, oxygen-containing compounds, sulfur or sulfur compounds or organic halides.

Processes for adsorption and adsorptive purification are described, for example, in W. Kast, Adsorption aus der Gasphase, V C H, Weinheim (1988). The use of zeolitic adsorbents is described in D. W. Breck, Zeolite Molecular Sieves, Wiley, N.Y. (1974).

The removal of specifically acetaldehyde from $C_3$–$C_{15}$-hydrocarbons in the liquid phase can be carried out as described in EP-A-0 582 901.

Selective Hydrogenation of Crude $C_4$ Fraction

In a two-stage process, butadiene (1,2- and 1,3-butadiene) present in the crude $C_4$ fraction from a steam cracker or a refinery is selectively hydrogenated first, after which alkynes or alkenynes present in the $C_4$ fraction are selectively hydrogenated. The $C_4$ stream from a refinery can also, in one embodiment, be fed directly to the second step of the selective hydrogenation.

The first hydrogenation step is preferably carried out over a catalyst comprising from 0.1 to 0.5% by weight of palladium on aluminum oxide as support. The reaction is carried out in the gas/liquid phase in a fixed bed (downflow mode) using a liquid circuit. The hydrogenation is carried out at from 40 to 80° C. and a pressure of from 10 to 30 bar, a molar ratio of hydrogen to butadiene of from 10 to 50 and an LHSV of up to 15 $m^3$ of fresh feed per $m^3$ of catalyst per hour and a ratio of recycle to feed stream of from 5 to 20.

The second hydrogenation step is preferably carried out over a catalyst comprising from 0.1 to 0.5% by weight of palladium on aluminum oxide as support. The reaction is carried out in the gas/liquid phase in a fixed bed (downflow mode) using a liquid circuit. The hydrogenation is carried out at from 50 to 90° C. and a pressure of from 10 to 30 bar, a molar ratio of hydrogen to butadiene of from 1.0 to 10 and an LHSV of from 5 to 20 $m^3$ of fresh feed per $m^3$ of catalyst per hour and a ratio of recycle to feed stream of from 0 to 15.

The hydrogenation is carried out under "low ISOM" conditions under which very little, if any, C=C isomerization of 1-butene to 2-butene occurs. The residual butadiene content can be from 0 to 50 ppm, depending on the severity of the hydrogenation conditions.

The reaction product obtained in this way is referred to as raffinate I and comprises, apart from isobutene, 1-butene and 2-butene in a molar ratio of from 2:1 to 1:10, preferably from 2:1 to 1:2.

Alternative: Removal of Butadiene from Crude $C_4$ Fraction by Extraction

The extraction of butadiene from crude $C_4$ fraction is carried out according to BASF technology using N-methylpyrrolidone.

The reaction product from the extraction is, in one embodiment of the invention, fed to the second step of the above-described selective hydrogenation in order to remove residual amounts of butadiene, with care having to be taken to ensure that little if any isomerization of 1-butene to 2-butene occurs.

Removal of Isobutene via Etherification with Alcohols

In the etherification step, isobutene is reacted with alcohols, preferably with isobutanol, over an acid catalyst, preferably over an acid ion exchanger, to form ethers, preferably isobutyl tert-butyl ether. In one embodiment of the invention, the reaction is carried out in a three-stage reactor cascade in which the reaction mixture flows from the top downward through flooded fixed-bed catalysts. In the first reactor, the inlet temperature is from 0 to 60° C., preferably from 10 to 50° C.; the outlet temperature is from 25 to 85° C., preferably from 35 to 75° C., and the pressure is from 2 to 50 bar, preferably from 3 to 20 bar. At a ratio of isobutanol to isobutene of from 0.8 to 2.0, preferably from 1.0 to 1.5, the conversion is from 70 to 90%.

In the second reactor, the inlet temperature is from 0 to 60° C., preferably from 10 to 50° C.; the outlet temperature is from 25 to 85° C., preferably from 35 to 75° C., and the pressure is from 2 to 50 bar, preferably from 3 to 20 bar. The total conversion over the two stages is increased to from 85 to 99%, preferably from 90 to 97%.

In the third and largest reactor, equilibrium conversion is achieved at equal inlet and outlet temperatures of from 0 to 60° C., preferably from 10 to 50° C. The etherification and separation of the ether formed is followed by ether cleavage: the endothermic reaction is carried out over acid catalysts, preferably over acidic heterogeneous catalysts, for example phosphoric acid on an $SiO_2$ support, at an inlet temperature of from 150 to 300° C., preferably from 200 to 250° C., and an outlet temperature of from 100 to 250° C., preferably from 130 to 220° C.

When using FCC $C_4$ fraction, it has to be expected that about 1% by weight of propane, about 30–40% by weight of isobutene and about 3–10% of $C_5$-hydrocarbons may be introduced, and these can adversely affect the subsequent process sequence. Accordingly, the possibility of removing these components by distillation is provided for in the work-up of the ether.

The reaction product obtained in this way, referred to as raffinate II, has a residual isobutene content of from 0.1 to 3% by weight.

If relatively large amounts of isobutene are present in the product, for example when using FCC $C_4$ fractions or when isobutene is removed by acid-catalyzed polymerization to polyisobutene (partial conversion), the remaining raffinate stream can, according to one embodiment of the invention, be subjected to a distillation before further processing.

Purification of the Raffinate II Stream Over Adsorbent Materials

The raffinate II stream obtained after the etherification/polymerization (or distillation) is purified over at least one guard bed comprising high surface area aluminum oxides, silica gels, aluminosilicates or molecular sieves. The guard bed serves to dry the $C_4$ stream and to remove substances which can act as catalyst poisons in the subsequent metathesis step. Preferred adsorbent materials are Selexsorb CD and CDO and 3 Å and NaX molecular sieves (13X). Purification is carried out in drying towers at temperatures and pressures which are chosen so that all components are present in the liquid phase. If desired, the purification step is used for preheating the feed to the subsequent metathesis step.

The remaining raffinate II stream is virtually free of water, oxygen-containing compounds, organic chlorides and sulfur compounds.

When the etherification step is carried out using methanol to prepare MTBE, the formation of dimethyl ether as secondary component may make it necessary to combine a plurality of purification steps or to use them sequentially.

To maximize the yield of 2-pentene and 3-hexene, the following variants of the process of the present invention, which are shown in simplified schematic form in FIG. 1, FIG. 2 and FIG. 3, are preferred. In the interests of clarity, the reactions are in each case described without significant amounts of isobutene in the $C_4$ feed. In the figures:

$C_2^=$ = ethane
$C_3^=$ = propene
$C_4^=$ = 1- and 2-butene
$C_4^-$ = n- and i-butane
$C_5^=$ = 2-pentene
$C_6^=$ = 3-hexene
$C_4$-Re = $C_4$ recycle
n-Bu = n-butenes
$C_{4/5}$-Re = $C_{4/5}$ recycle
$C_5$-Re = $C_5$ recycle Metathesis with 2-stage Distillation and Partial $C_4$ Recycle Isolation of 2-pentene and 3-hexene (FIG. 1)

Figure 1:
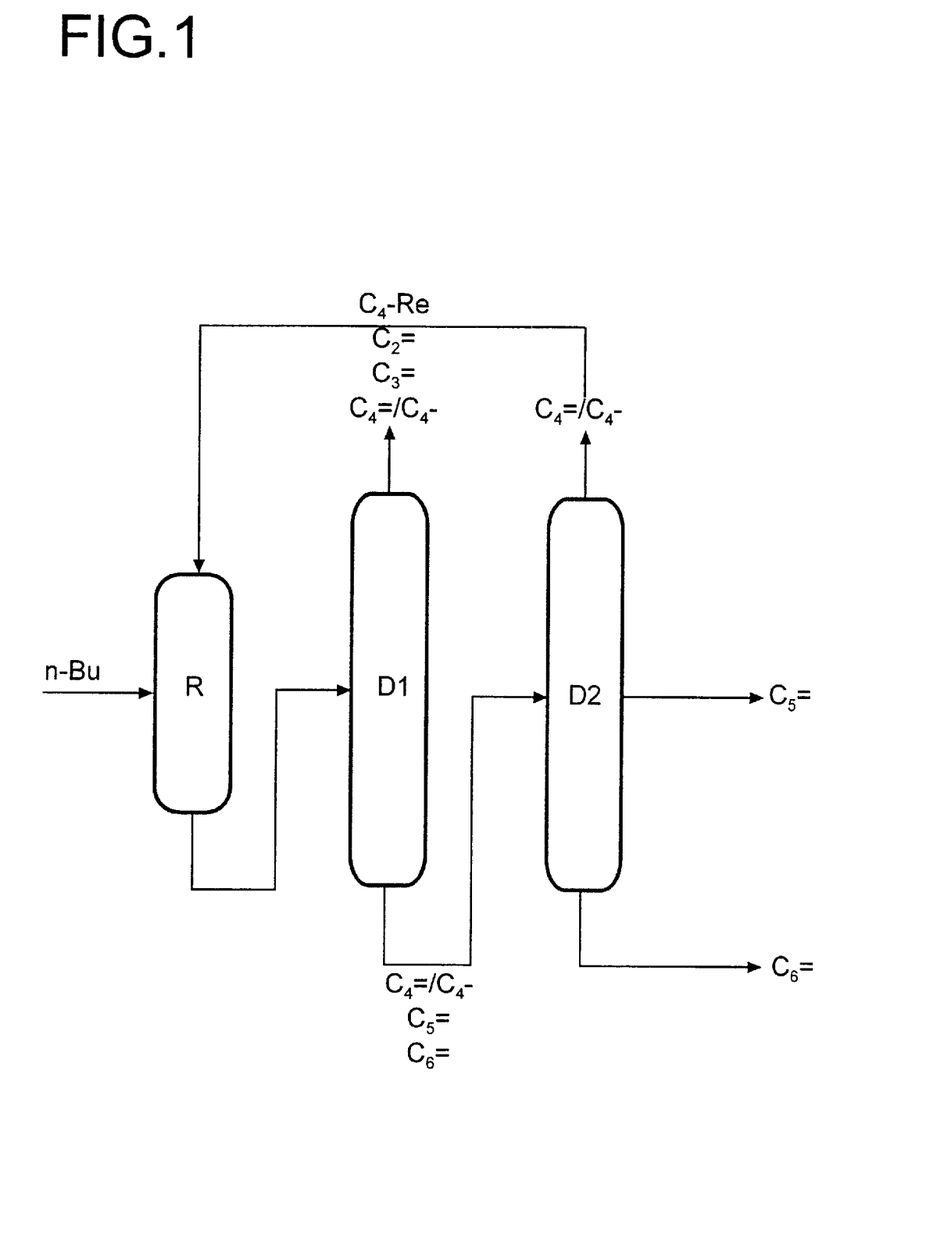

The product stream from the metathesis reactor R, comprising $C_2$–$C_6$-olefins and butanes, is fractionated in the distillation D1 to give a fraction comprising ethene, propene and from 0 to 50% of unreacted butenes and butanes, which may, if desired, be fed to the work-up sequence of a cracker, and a high boiler fraction comprising residual $C_4$ and the 2-pentene and 3-hexene formed. The latter fraction is distilled in a column D2 to give 2-pentene at the side offtake and 3-hexene. Both streams are obtained in a purity of >99%. The $C_4$ fraction is taken off at the top and recirculated to the metathesis reactor R. Column D2 can also be designed as a separation plate column. The reactor R and the column D1 can be coupled to form a reactive distillation unit.

To increase the yield of $C_5/C_6$-olefins, the top product from the distillation column D1 can, if required, be recirculated to the metathesis reactor R.

Figure 2:
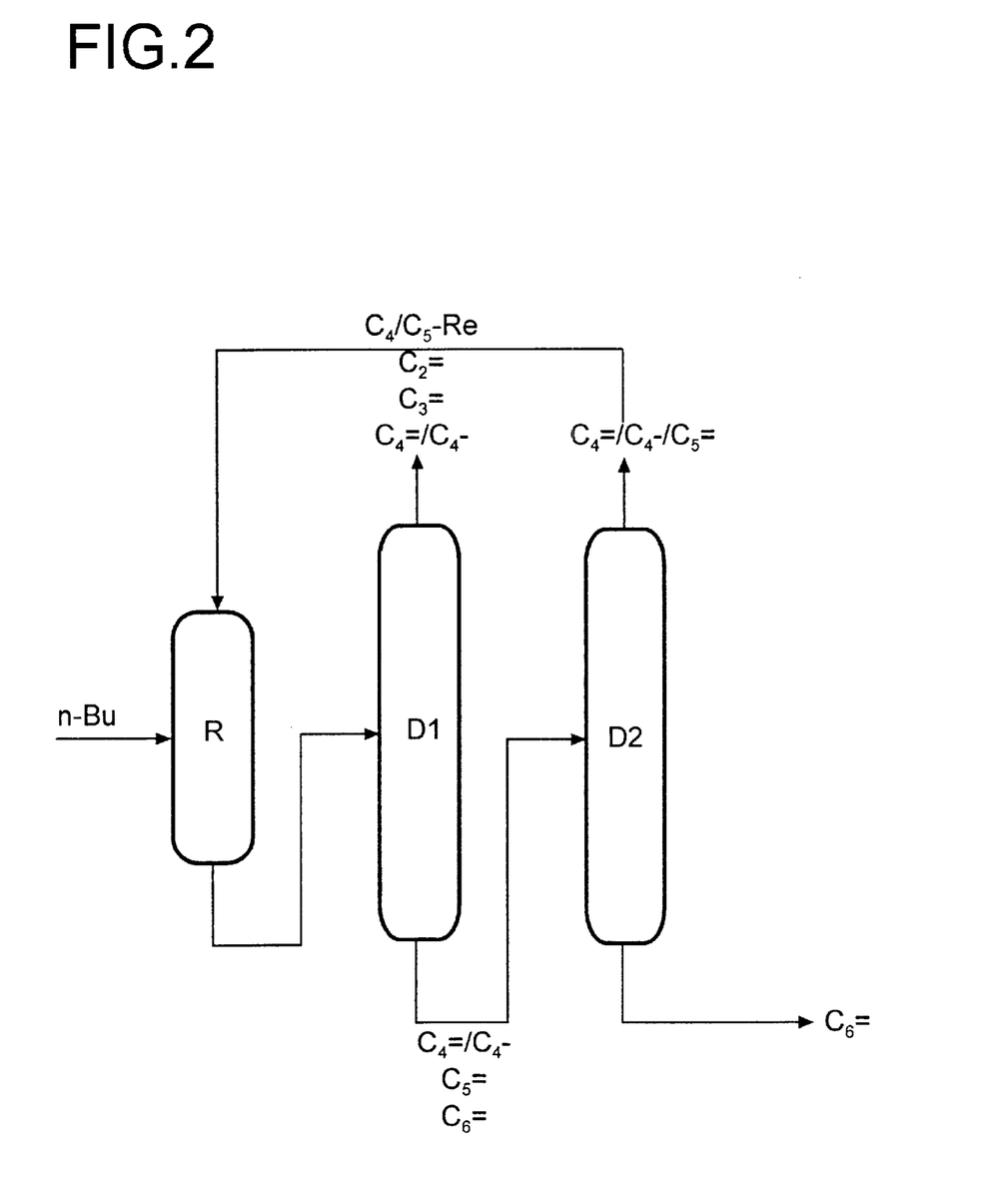

Metathesis Step with 2-stage Distillation and Partial $C_4$- and $C_5$-recycle Maximization of the Hexene Yield (FIG. 2)

The product stream from the metathesis reactor R, comprising $C_2$–$C_6$-olefins and butanes, is fractionated in the distillation D1 to give a fraction comprising ethene, propene and from 0 to 50% of unreacted butenes and butanes, which may be fed to the work-up sequence of a cracker, and a high boiler fraction comprising residual $C_4$ and the 2-pentene and 3-hexene formed. The latter fraction is distilled in a column D2 to obtain 3-hexene which is isolated in a purity of >99%. The $C_4$ fraction together with pentene is taken off at the top and recirculated to the metathesis reactor R. The reactor R and the columns D1 and D2 can be coupled to form a reactive distillation unit.

Figure 3:
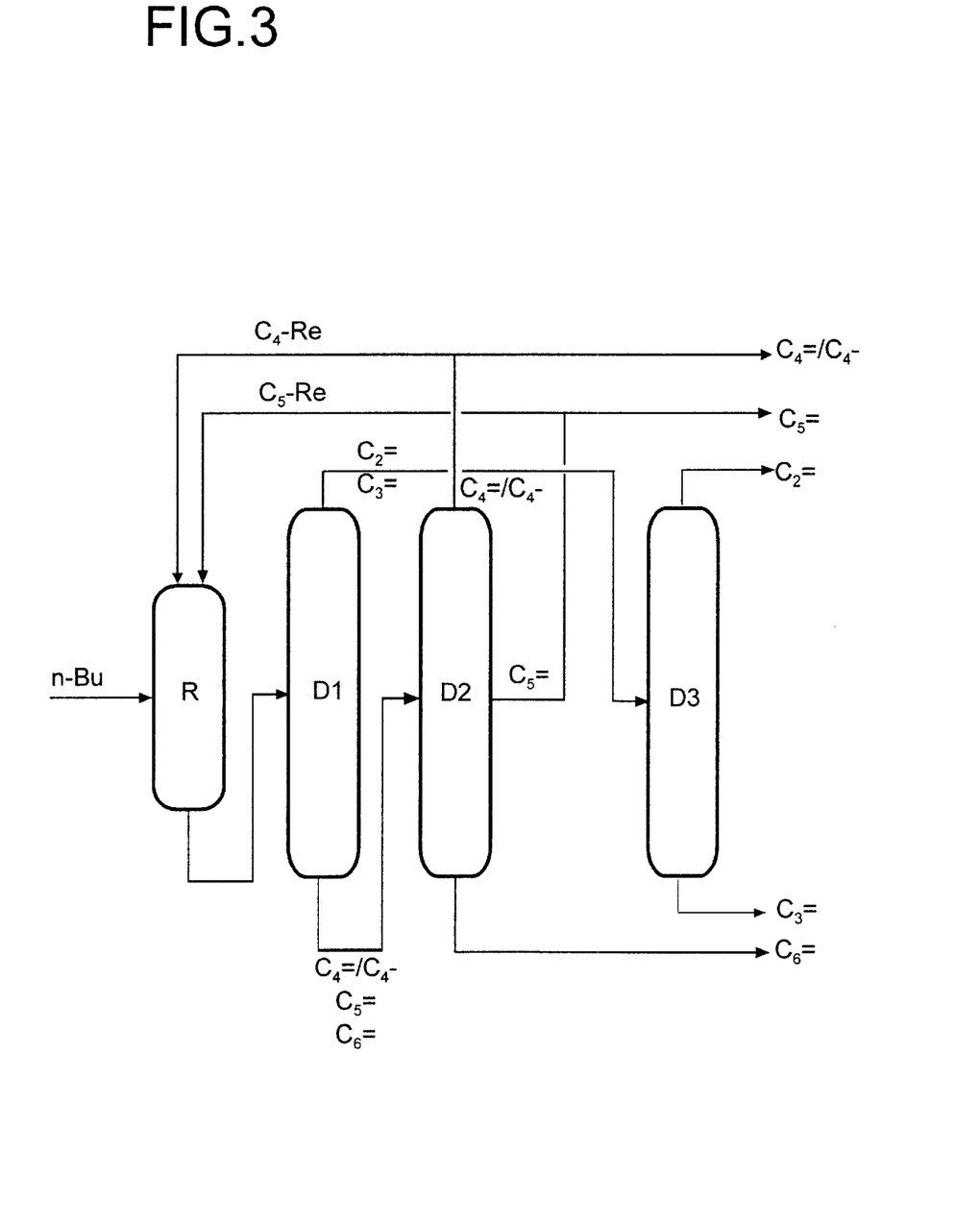

Metathesis Step with 3-stage Distillation/Partial $C_4$- and $C_5$-recycle to Maximize the Hexene Yield (FIG. 3)

The product stream from the metathesis reactor R, comprising $C_2$–$C_6$-olefins and butanes, is fractionated in the distillation D1 to give a low boiler fraction comprising ethene and propene, which can either be fed to the work-up sequence of a cracker or, preferably, is separated into the pure components ethene and propene in a further distillation column D3, and a high boiler fraction comprising $C_4$-olefins and butanes and the 2-pentene and 3-hexene formed. The latter fraction is fractionated in a column D2, which may, if desired, be designed as a side offtake column or dividing wall column, to give a low boiler fraction comprising $C_4$-olefins and butanes, all or part of which can be recirculated to the metathesis step, an intermediate boiler fraction preferably comprising 2-pentene, all or part of which can be recirculated to the metathesis step, and a high boiler fraction comprising the desired product 3-hexene (purity of >99%), which is discharged.

As catalysts, preference is given to heterogeneous rhenium catalysts known from the literature, for example $Re_2O_7$ on $\gamma$-$Al_2O_3$ or on mixed supports such as $SiO_2/Al_2O_3$, $B_2O_3/SiO_2/Al_2O_3$ or $Fe_2O_3/Al_2O_3$ having differ Regardless of the support chosen, the rhenium oxide content is from 1 to 20%, preferably from 3 to 10%.

The catalysts are used in freshly calcined form and require no further activation (e.g. by means of alkylating agents). Deactivated catalyst can be regenerated a number of times by burning off coke residues at above 400° C. in a stream of air and cooling under an inert gas atmosphere.

Less suitable, but nevertheless able to be used according to the present invention, are homogeneous catalysts which are sometimes more active but have a significantly shorter operating life:

K. J. Ivin, J. Organomet. Catal. A: Chemical 1998, 133, 1–16; K. J. Ivin, I. C. Mol, Olefin Metathesis and Metathesis Polymerization, $2^{nd}$ edition, Academic Press, New York, 1996; G. W. Parshall, S. D. Ittel, Homogeneous, Catalysis, $2^{nd}$ edition, 1992, John Wiley & Sons, New York, Chichester, Brisbane, Toronto, Singapore, p. 217 ff; R. H. Grubbs in Prog. Inorg. Chem., S. Lippard (editor), John Wiley & Sons, New York, 1978, Vol. 24, 1–50; R. H. Grubbs in Comprehensive Organomet. Chem., G. Wilkinson (editor), Pergamon Press, Ltd., New York, 1982, Vol. 8, 499–551; D. S. Breslow, Prog. Polym. Sci. 1993, Vol. 18, 1141–1195, and also homogeneous metathesis catalysts which are stable to protic media and to atmospheric oxygen, for example the defined ruthenium-alkylidene compounds of the formula $RuX_2(=CHR)(PR'_3)_2$ (R=R'=alkyl,aryl) described by R. H. Grubbs et al. in WO 93/20111, WO 96/04289, WO 96/06185, WO 97/03096 and WO 98/21214 and also mixtures generated in situ from $[Ru(n^6\text{-aryl})X_2]_2$, phosphines $PR_3$ and diazo compounds $RCHN_2$, whose suitability as metathesis catalysts has been reported by A. F. Noels in J. Chem. Soc., Chem. Commun. 1995, 1127–1128. In comparison, heterogeneous catalysts, in particular molybdenum oxides, tungsten oxides and rhenium oxides on inorganic oxidic supports, which may have been pretreated with alkylating agents, are frequently found to be more sensitive to impurities in the feed. Their advantage over homogeneous catalysts having higher activity is the very simple catalyst regeneration which is usually carried out by burning off coke residues in a stream of air. Comparison of the heterogeneous catalysts with one another shows that $Re_2O_7/Al_2O_3$ is active under very mild reaction conditions (T=20–80° C.) while $MO_3/SiO_2$ (M=Mo, W) become active only at temperatures above 100–150° C. and it is therefore possible for C=C double bond isomerizations to occur as secondary reactions.

Further catalysts which may be mentioned are:

$WO_3/SiO_2$, prepared from $(C_5H_5)W(CO)_3Cl$ and $SiO_2$ in J. Mol Catal. 1995, 95, 75–83;

3-component system comprising $[MO(NO)_2(OR)_2]n$, $SnEt_4$ and $AlCl_3$ in J. Mol. Catal. 1991, 64, 171–178 and J. Mol. Catal 1989, 57, 207–220;

nitridomolybdenum(VI) complexes from highly active precatalysts in J. Organomet. Chem. 1982, 229, $C_{19}$–$C_{23}$;

heterogeneous $SiO_2$-supported $MoO_3$ and $WO_3$ catalysts in J. Chem. Soc., Faraday Trans./1982, 78, 2583–2592;

supported Mo catalysts in J. Chem. Soc., Faraday Trans./ 1981, 77, 1763–1777;

active tungsten catalyst precursor in J. Am. Chem. Soc. 1980, 102(21), 6572–6574;

acetonitrile(pentacarbonyl)tungsten in J. Catal. 1975, 38, 482–484;

trichloro(nitrosyl)molybdenum(II) as catalyst precursor in Z. Chem. 1974, 14, 284–285;

W(CO)$_5$PPH$_3$/EtAlCl$_2$ in J. Catal. 1974, 34, 196–202;

WCl$_6$/n-BuLi in J. Catal 1973, 28, 300–303;

WCl$_6$/n-BuLi in J. Catal. 1972, 26, 455–458;

FR 2 726 563 O$_3$ReO[Al(OR)(L)xO]nReO$_3$ where R=C$_1$–C$_{40}$-hydrocarbon, n=1–10, x=0 or 1 and L=solvent, EP-A-191 0 675, EP-A-129 0 474, BE 899897 catalyst systems comprising tungsten, 2 substituted phenoxide groups and four other ligands, including a halogen, alkyl or carbene group, FR 2 499 083 catalyst system comprising a tungsten, molybdenum or rhenium oxotransition metal complex with a Lewis acid;

U.S. Pat. No. 4,060,468 catalyst system comprising a tungsten salt, an oxygen-containing aromatic compound, e.g. 2,6-dichlorophenol, and possibly molecular oxygen;

BE 776,564 catalyst system comprising a transition metal salt, an organometallic compound and an amine.

To improve the cycle time of the catalysts used, especially the supported catalysts, purification of the feed using adsorber beds (guard beds) is advisable. The guard bed serves to dry the C$_4$ stream and to remove substances which could act as catalyst poisons in the subsequent metathesis step. The preferred adsorbent materials are Selexsorb CD and CDO and also 3 Å and NaX molecular sieves (13X). The purification is carried out in drying towers at temperatures and pressures which are preferably chosen so that all components are in the liquid phase. The purification step may also be used for preheating the feed to the subsequent metathesis step. It can be advantageous to combine a plurality of purification steps with one another or to use them sequentially.

The pressure and temperature in the metathesis step are chosen so that all reactants are present in the liquid phase (usually from 0 to 150° C., preferably from 20 to 80° C.; p=2–200 bar). However, as an alternative, it may be advantageous, particularly in the case of feed streams having a relatively high isobutene content, to carry out the reaction in the gas phase and/or to use a catalyst which has a relatively low acidity.

In general, the reaction is complete after from 1 s to 1 h, preferably after from 30 s to 30 min. It can be carried out continuously or batchwise in reactors such as pressure gas vessels, flow tubes or reactive distillation apparatuses, with preference being given to flow tubes.

EXAMPLES

Example 1

Continuous Experiment of the Two-stage Selective Hydrogenation of Crude C$_4$ Fraction Crude C$_4$ fraction having a composition of 43.7% of butadiene (including butenyne and butyne), 14.3% of 1-butene, 7.8% of 2-butenes and 7.2% of n-butane is reacted with 175 standard 1/h of hydrogen over 0.3% Pd/Al$_2$O$_3$ heterogeneous catalyst in a continuous flow tube reactor at a fresh feed flow of 1 kg/h of crude C$_4$ fraction and a circulation of 8.2 kg/h at an LHSV of 9.0 h$^{-1}$ at a reactor inlet temperature of 20° C. At a butadiene conversion of 95.2%, the first stage of the selective hydrogenation under these conditions achieves a total butene selectivity of 99.6% and a 1-butene selectivity of 56.5%.

A typical reaction product from the first stage of the selective hydrogenation, comprising 0.61% of butadiene (including butenyne and butyne), 26.9% of 1-butene, 14.9% of 2-butenes and 11.6% of n-butane, is reacted with 16 standard 1/h of hydrogen over 0.3% Pd/Al$_2$O$_3$ heterogeneous catalyst (H0-13L) in a continuous flow tube reactor at a fresh feed flow of 2.2 kg/h of reaction product from the first stage and a circulation of 4.0 kg/h at an LHSV of 20 h$^{-1}$ at a reactor inlet temperature of 60° C. and a reactor outlet temperature of 70° C. At a butadiene conversion of 99.2% and a 1-butene yield of 58.2%, a raffinate I stream having a residual butadiene content of 48 ppm was obtained under these conditions.

Example 2

Continuous Experiment on the Removal of Isobutene by Etherification with Isobutanol In a three-stage reactor cascade, raffinate I and isobutanol are passed from the top downward through a flooded fixed bed of acid ion exchanger, with the ratio of isobutanol to isobutene in the feed being set to 1.2. The reactor inlet temperature is 40° C., the reactor outlet temperature is 65° C. and the reaction pressure is 8 bar. The isobutene conversion after the first stage is measured as 85%. In the second, similarly dimensioned reactor, the conversion is increased to 95% at a reactor inlet temperature of 40° C., a reactor outlet temperature of 50° C. and a reaction pressure of 8 bar. In the third, significantly larger reactor, equilibrium conversion is achieved at a reactor inlet temperature and reactor outlet temperature of 40° C. in each case and a reaction pressure of 8 bar. The raffinate stream remaining under these conditions after removal of isobutyl tert-butyl ether by distillation has a residual isobutene content of 0.7%.

Example 3

Continuous Experiment on the Single-stage Metathesis of Raffinate II

After feed purification over an adsorber bed of molecular sieve 13X, a C$_4$ fraction comprising 43.5% of 1-butene, 36.2% of 2-butene, 2.0% of isobutene and 18.3% of butanes is passed continuously at a mass flow of 1300 g/h and a residence time of 3 minutes through a flow tube containing Re$_2$O$_7$/Al$_2$O$_3$ heterogeneous catalyst at 40° C. and 10 bar (liquid phase). The reaction product is fractionated in a two-stage distillation sequence, with a C$_2$/C$_3$/C$_4$ low boiler phase comprising 1.2% of ethene, 38.7% of propene, 31.3% of butenes, 2.9% of isobutene and 25.9% of butanes being taken off at the top of the first column at 10 bar. The bottoms comprising 28.0% of butenes, 1.3% of isobutene, 20.4% of butanes, 27.8% of 2-pentene and 21.9% of 3-hexene are subsequently passed to a second column operated at 2 bar, in which the C$_4$/C$_5$ low boiler fraction is taken off at the top and is all recirculated to the metathesis reaction. The high boiler fraction obtained at the bottom comprises 99.5% of 3-hexene. The percentages are in each case by mass. The butene conversions determined are 91% in respective of 1-butene and 50% in respect of 2-butene. The space-time yields determined were, on average, 700 g/l×h of propene and 760 g/l×h of 3-hexene.

We claim:

1. A process for preparing C$_5$-/C$_6$-olefins and propene from steam cracker or refinery C$_4$ streams, comprising the substeps (1) removal of butadiene and acetylenic compounds by, optionally, extracting butadiene with a butadiene-selective solvent and subsequently or alternatively selectively hydrogenating butadienes and acetylenic impurities present in the residual steam cracker or refinery C4 streams to give a reaction product comprising n-butenes and isobutene and essentially no butadienes and acetylenic compounds, (2) removing isobutene by either oligomerization or polymerization, or by reacting the reaction product from the preceding stage with an alcohol in the presence of an acid catalyst to give an ether, and separating off the ether and the alcohol either simultaneously with or after the etherification to give a reaction product comprising n-butenes and optionally oxygen-containing impurities, where the ether formed is discharged or redissociated to obtain pure isobutene and the etherification step can be followed by a distillation step for separating off isobutene, where, optionally, $C_3$-, $i$-$C_4$- and $C_5$-hydrocarbons, introduced in a FCC fraction, are removed by distillation of the ether, (3) optionally removing the oxygen-containing impurities from the raffinate II stream from step (2) by treating the raffinate II stream with adsorber materials, (4) carrying out a metathesis reaction of the raffinate II stream from step (3) in the presence of a metathesis catalyst comprising at least one compound of a metal of transition group VIb, VIIb or VIII of the Periodic Table of the Elements so as to convert the 1-butane, 2-butene and isobutene present in the raffinate II stream into a mixture of $C_2$–$C_6$-olefins and butanes, (5) firstly fractionating the product stream of step (4) by distillation to give a low boiler fraction A comprising $C_2$–$C_4$-olefins and butanes or $C_2$–$C_3$-olefins, which is discharged, and a high boiler fraction comprising $C_4$–$C_6$-olefins and butanes, (6) subsequently fractionating the high boiler fraction from step (5) by distillation to give a low boiler fraction B comprising butenes and butanes, an intermediate boiler fraction C comprising pentene and methylbutene and a high boiler fraction D comprising hexene and methylpentene, (7) where all or part of the fractions B and/or C are recirculated to the process step 4) and the fraction D is discharged as product.

2. A process as claimed in claim 1, wherein the $C_5$–$C_5$-olefins and propene are obtained from a FCC plant or in the dehydrogenation of butane.

3. A process as claimed in claim 1, wherein the metathesis reaction is carried out in the presence of heterogeneous metathesis catalysts selected from the group consisting of transition metal compounds of metals of groups VIb, VIIb and VIII of the Periodic Table of the Elements applied to inorganic supports.

4. A process as claimed in claim 3, wherein the metathesis catalyst used is rhenium oxide on γ-aluminum oxide or on $Al_2O_3/B_2O_3/SiO_2$ mixed supports.

5. A process as claimed in claim 1, wherein the substep of selective hydrogenation of butadienes and acetylenic impurities present in the steam cracker or refinery C4 streams is carried out in two stages by bringing the steam cracker or refinery C4 streams into contact with a catalyst comprising at least one metal selected from the group consisting of nickel, palladium and platinum on a support, at from 20 to 200° C., a pressure of from 1 to 50 bar, a volume flow of from 0.5 to 30 m³ of fresh feed per m³ of catalyst per hour and a ratio of recycle to feed stream of from 0 to 30 at a molar ratio of hydrogen to diolefins of from 0.5 to 50 to give a reaction product in which, apart from isobutene, the n-butenes 1-butene and 2-butene are present in a molar ratio of from 2:1 to 1:10, and in which essentially no diolefins and acetylenic compounds are present.

6. A process as claimed in claim 1, wherein the substep of butadiene extraction from crude $C_4$ fraction is carried out using a butadiene-selective solvent selected from the group consisting of acetone, furfural, acetonitrile, dimethylacetamide, dimethylformamide and N-methylpyrrolidone to give a reaction product in which the n-butenes 1-butene and 2-butene are present in a molar ratio of from 2:1 to 1:10.

7. A process as claimed in claim 1, wherein the substep of isobutene etherification is carried out in a three-stage reactor cascade using methanol or isobutanol in the presence of an acid ion exchanger, in which the extraction mixture flows from the top downward through a flooded fixed-bed catalyst, where the reactor inlet temperature is from 0 to 600° C., the outlet temperature is from 25 to 85° C., the pressure is from 2 to 50 bar and the ratio of isobutanol to isobutene is from 0.8 to 2.0, and the total conversion corresponds to the equilibrium conversion.

8. A process as claimed in claim 1, wherein the substep of isobutene removal proceeds by oligomerization or polymerization of isobutene starting from the reaction product obtained from the above-described step of butadiene extraction and/or selective hydrogenation and in the presence of a catalyst selected from the group consisting of heterogeneous catalysts comprising an oxide of a metal of transition group VIb of the Periodic Table of the Elements on an acidic inorganic support to produce a stream having a residual isobutene content of less than 15%.

9. A process as claimed in claim 1, wherein the steam cracker or refinery C4 streams are subjected to a first substep of feed purification which is carried out over at least one guard bed comprising a member selected from the group consisting of high surface area aluminum oxides, silica gels, aluminosilicates and molecular sieves.

* * * * *